(12) United States Patent
Perkins et al.

(10) Patent No.: US 12,063,897 B2
(45) Date of Patent: Aug. 20, 2024

(54) ALGAE BIOFUEL PRODUCTION AND SYSTEMS, METHODS, AND DEVICES RELATED THERETO

(71) Applicant: ExxonMobil Technology and Engineering Company, Annandale, NJ (US)

(72) Inventors: David L. Perkins, Easton, PA (US); Amy C. Clingenpeel, Washington, NJ (US); Mark A. Deimund, Jersey City, NJ (US)

(73) Assignee: EXXONMOBIL TECHNOLOGY AND ENGINEERING COMPANY, Spring, TX (US)

(*) Notice: Subject to any disclaimer, the term of this patent is extended or adjusted under 35 U.S.C. 154(b) by 796 days.

(21) Appl. No.: 17/157,068

(22) Filed: Jan. 25, 2021

(65) Prior Publication Data

US 2022/0232788 A1    Jul. 28, 2022

(51) Int. Cl.
*A01G 33/00* (2006.01)
*C12N 1/12* (2006.01)
*G01N 33/18* (2006.01)

(52) U.S. Cl.
CPC ............... *A01G 33/00* (2013.01); *C12N 1/12* (2013.01); *G01N 33/1833* (2013.01); *G01N 33/1846* (2013.01)

(58) Field of Classification Search
CPC ...... A01G 33/00; C12N 1/12; G01N 33/1833; G01N 33/1846
See application file for complete search history.

(56) References Cited

U.S. PATENT DOCUMENTS

| | | | |
|---|---|---|---|
| 8,908,165 B2 | 12/2014 | Tunheim et al. | |
| 9,103,716 B2 | 8/2015 | Tunheim et al. | |
| 9,170,208 B2 | 10/2015 | Tunheim et al. | |
| 9,206,386 B2 | 12/2015 | Tunheim et al. | |
| 9,261,461 B2 | 2/2016 | Tunheim et al. | |
| 2013/0162999 A1* | 6/2013 | Myrick | G01J 3/28 356/402 |
| 2013/0284904 A1* | 10/2013 | Freese | G01N 21/274 250/214 DC |

\* cited by examiner

*Primary Examiner* — Jamil Ahmed
(74) *Attorney, Agent, or Firm* — Shook, Hardy & Bacon L.L.P.

(57) ABSTRACT

Devices, methods, and systems employing a multivariate optical computing sensor comprising a multivariate optical element calibrated to independently measure an electromagnetic spectral pattern of a cultivation characteristic of an algae strain in a cultivating algae water slurry and a detector for receiving output signals indicative of the cultivation characteristic. The cultivation characteristic may include, for example, total organic carbon, total carbohydrate, or fatty acid methyl esters.

20 Claims, 6 Drawing Sheets

ALGAE BIOFUEL PRODUCTION AND SYSTEMS, METHODS, AND DEVICES RELATED THERETO

FIELD OF THE INVENTION

The present disclosure relates to algae biofuel production and systems, methods, and devices related thereto and, more particularly, to the use of in-situ multivariate optical computing to optimize algae biofuel production.

BACKGROUND OF THE INVENTION

Concerns about climate change, carbon dioxide ($CO_2$) emissions, and depleting mineral oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources.

Algae are photoautotrophic organisms that can survive, grow, and reproduce with energy derived from the sun through the process of photosynthesis. Photosynthesis is a carbon recycling process through which inorganic $CO_2$ combines with solar energy, other nutrients, and cellular biochemical processes to output gaseous oxygen and to synthesize carbohydrates and other compounds critical to the life of the algae.

To produce algal biomass, algae cells are generally grown in a water slurry comprising water and nutrients. The algae may be cultivated in indoor or outdoor environments, and in closed or open cultivation systems. Closed cultivation systems include photobioreactors, which utilize natural or artificial light to grow algae in an environment that is generally isolated from the external atmosphere. Such photobioreactors may be in a variety of shaped configurations, but are typically tubular or flat paneled. Open cultivation systems include natural and artificial ponds that utilize sunlight to facilitate photosynthesis. Artificial ponds are generally more preferred for industrial, scaled-up cultivation and are often shaped in circular (oval) or raceway-shaped configurations.

Cultivated algae biologically produce sugars (e.g., carbohydrates) and can be harvested and processed for conversion of the sugars into valuable biofuels, such as fatty acid methyl ester and/or other fatty acids. However, during cultivation, particularly at the industry scale, various characteristics of the cultivation system may drastically influence the growth characteristics of the algae therein, thus reducing the quality and/or quantity of any obtained sugars for producing biofuel. Traditionally, these cultivation characteristics have been measured by sampling a cultivating water slurry and testing at an offsite facility, which often can take up to or greater than three (3) days turnaround. After the turnaround time lag, the status of the cultivation characteristics may have become altered, such that the quality and/or quantity of biofuel to be obtained from the algae are reduced, which can significantly affect resource, economic, and time costs to an algae biofuel producing facility.

Because algal biomass produces valuable commodities, including sustainable biofuels, real-time or near real-time testing of one or more cultivation characteristics that affect cultivated algae growth is desirable.

SUMMARY OF THE INVENTION

The present disclosure relates to algae biofuel production and systems, methods, and devices related thereto and, more particularly, to the use of in-situ multivariate optical computing to optimize algae biofuel production.

In some aspects, a multivariate optical computing sensor is disclosed. The multivariate optical computing sensor includes a first multivariate optical element calibrated to independently measure an electromagnetic spectral pattern of a first cultivation characteristic of an algae strain in a cultivating algae water slurry and a detector for receiving modified electromagnetic radiation from the first multivariate optical element and generating an output signal indicative of the first cultivation characteristic.

In some aspects, a method is disclosed for deploying a multivariate optical computing sensor into a cultivating algae water slurry comprising an algae strain. The multivariate optical computing sensor includes a first multivariate optical element calibrated to independently measure an electromagnetic spectral pattern of a first cultivation characteristic of an algae strain in a cultivating algae water slurry and a detector for receiving modified electromagnetic radiation from the first multivariate optical element and generating an output signal indicative of the first cultivation characteristic. Using the first multivariate optical element, electromagnetic radiation is received from the cultivating algae water slurry and the electromagnetic spectral pattern of the first cultivation characteristic is distinguished, thereby producing the modified electromagnetic radiation. Using the detector, the modified electromagnetic radiation is detected and output signals indicative of the first cultivation characteristic are generated.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION OF THE INVENTION

The present disclosure relates to algae biofuel production and systems, methods, and devices related thereto and, more particularly, to the use of in-situ multivariate optical computing to optimize algae biofuel production.

Biofuel production from cultivated algae slurries offers sustainable energy solutions to reduce reliance on fossil fuels and reduce greenhouse gas emissions. Other non-oil-based products can additionally be derived from algal biomass. To accomplish substantial economic, environmental, and societal impact, algae must be cultivated in large-scale, industrial-sized systems. However, various characteristics within a cultivating algae water slurry may be reduced, consumed, or otherwise influenced by cultivating algae, thereby limiting or hindering the quality and/or quantity of sugars for the production of biofuel. Traditional solutions include sampling and offsite testing, which may result in substantial lag time between the testing and receipt of the results, thereby providing an inaccurate capture of cultivation characteristics of the current algae water slurry.

Unlike traditional methods, various aspects of the present disclosure provide systems, methods, and devices to perform in-situ multivariate optical computing to measure one or more critical cultivation characteristics of a cultivating algae water slurry to optimize downstream algae biofuel production. The in-situ determination of these critical cultivation characteristics allows immediate or near-immediate corrective action (unlike traditional methods) to augment the characteristics of a cultivating algae water slurry, as needed, thereby optimizing biofuel productivity of an algae production facility. Moreover, the in-situ multivariate optical computing provided in the present disclosure may be customized for particular algae strains. Once optimized, and to the proper confluency (growth amount), the algae from the algae water slurry can be harvested and processed to obtain desired biofuel.

As used herein, the term "algae slurry" or "algae water slurry," and grammatical variants thereof, refers to a flowable liquid comprising at least water, algae cells, and algae nutrient media (e.g., phosphorous, nitrogen, and optionally additional elemental nutrients).

Algal sources for preparing the algae slurry include, but are not limited to, unicellular and multicellular algae. Examples of such algae can include, but are not limited to, a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In some examples, algae can be of the classes Chlorophyceae and/or Haptophyta. Examples, as well as additional or alternative algal sources may include one or more (including all) of *Achnanthes, Agmenellum, Amphiprora, Amphora, Anabaena, Anabaenopsis, Anacystis, Ankistrodesmus, Aphanizomenon, Arthrospira, Asterocapsa, Asteromonas, Auxenochlorella, Boekelovia, Borodinella, Borzia, Botryococcus, Bracteococcus, Calothrix, Carteria, Chaetoceros, Chamaesiphon, Chlamydomonas, Chlorella, Chlorococcum, Chlorogloeopsis, Chlorogonium, Chroococcidiopsis, Chroococcus, Chroomonas, Chrysosphaera, Compactochlorella, Cricosphaera, Crinalium, Crypthecodinium, Cryptomonas, Cyanobacterium, Cyanobium, Cyanocystis, Cyanospira, Cyanothece, Cyclotella, Cylindrospermopsis, Cylindrospermum, Dactylococcopsis, Dermocarpella, Dunaliella, Ellipsoidon, Emiliania, Eremosphaera, Ernodesmius, Euglena, Fischerella, Fragilaria, Franceia, Fremyella, Geitleria, Geitlerinema, Gloeobacter, Gloeocapsa, Gloeothamnion, Gloeothece, Haematococcus, Halocafeteria, Halospirulina, Hymenomonas, Isochrysis, Iyengariella, Lepocinclis, Leptochlorella, Leptolyngbya, Limnothrix, Lyngbya, Marinichlorella, Microctinium, Microcoleus, Microcystis, Monoraphidium, Myxosarcina, Nannochloris, Nannochloropsis, Nanochlorum, Navicula, Neochloris, Nephrochloris, Nephroselmis, Nitzschia, Nodularia, Nostoc, Nostochopsis, Ochromonas, Oedogonium, Oocystis, Oscillatoria, Ostreococcus, Parachlorella, Pascheria, Pavlova, Phaeodactylum, Phagus, Phormidium, Picochlorum, Planktochlorella, Planktothrix, Platymonas, Pleurocapsa, Pleurochrysis, Pleurococcus, Prochlorococcus, Prochloron, Prochlorothrix, Prototheca, Pseudanabaena, Pseudochlorella, Pseudoneochloris, Pseudostaurastrum, Psuedochlorococcum, Pyramimonas, Pyrobotrys, Rivularia, Scenedesmus, Schizochlamydella, Schizothrix, Scytonema, Skeletonema, Spirulina, Spyrogyra, Stanieria, Starria, Stichococcus, Stigonema, Symploca, Synechococcus, Synechocystis, Tetrachlorella, Tetraselmis, Thalassiosira, Tolypothrix, Tribonema, Trichodesmium, Tychonema, Vaucheria, Viridiella, Volvox, Xenococcus,* and *Zoochlorella* algal species. Any combination of the aforementioned algae sources may additionally be used to prepare an algae slurry.

The water for use in preparing the algae slurry may be from any water source including, but not limited to, freshwater, brackish water, seawater, brine wastewater (treated or untreated), synthetic seawater (e.g., water with added salts), and any combination thereof. Generally, the water in an algae slurry contains one or more dissolved or undissolved electrolytes (e.g., salts) therein and are collectively referred to herein as "brine." As used herein, the term "brine," and grammatical variants thereof, with reference to a stream fed into the electrochemical cells of the present disclosure comprise at least 3% by weight of dissolved sodium and chlorine therein, such as in the range of about 3% to about 10% by weight of dissolved sodium and chlorine therein, encompassing any value and subset therebetween.

The algae nutrient media for use in forming an algae slurry may comprise at least nitrogen (e.g., in the form of ammonium nitrate or ammonium urea) and phosphorous. Other elemental micronutrients may also be included, such as potassium, iron, manganese, copper, zinc, molybdenum, vanadium, boron, chloride, cobalt, silicon, and the like, and any combination thereof.

As used herein, the term "cultivation vessel," "vessel," and grammatical variants thereof, refers to any of an open or closed algae cultivation system used for the growth of algal biomass, including bioreactors, photobioreactors, natural ponds, artificial ponds (e.g., raceway ponds), and the like, including combinations thereof.

As used herein, the term "critical cultivation characteristics," and grammatical variants thereof, refers to characteristics of a cultivating algae slurry including total organic carbon (TOC), total carbohydrate, fatty acid methyl esters (FAME), and any combination thereof. It should be appreciated, however, that while the current disclosure is described with reference to these critical cultivation characteristics, other cultivation characteristics may be tested using the systems, methods, and devices described herein. Those other cultivation characteristics may include, but are not limited to, carbohydrate concentration, lipid concentration, plant stress (Fv/Fm), ash free dry weight (biomass concentration, slurry pH, slurry temperature, slurry salinity, suspended solids, dissolved nitrogen, and the like, and any combination thereof.

As used herein, the term "multivariate optical computing" or "MOC," and grammatical variants thereof, refers to a compressed analytical sensing spectroscopic technique, which employs a multivariate optical element (MOE) encoded with an optical regression vector unique to a specific analyte or characteristic of interest. That is, the optical regression factor of the MOE may be fine-tuned (calibrated) to a specific electromagnetic spectral pattern of a specific analyte or characteristic of interest, such as the critical cultivation characteristics described herein. The "electromagnetic spectral patterns" of the MOE includes electromagnetic radiation waves having frequencies ranging from 1 hertz to $10^{25}$ hertz, including infrared, visible light, ultraviolet, X-rays, and gamma rays.

A device that employs MOC, using an MOE, may be referred to as a multivariate optical computing sensor or "MOC sensor." The MOC sensors of the present disclosure provide accurate compositional and/or physical analysis of at least one critical cultivation characteristic of at least one specific algae strain.

As provided above, various critical cultivation characteristics may influence algae growth and, thus, the subsequent quality and/or quantity of biofuel produced therefrom. TOC measurements may be indicative of the energetic value of an algal biomass and provide insight into to the carbon conversion efficiency within a cultivation system. Carbohydrates are the main substrate for the production of biofuel; accurate and timely quantification of total carbohydrate content can be used to alter conditions (e.g., nutrient conditions within a cultivating algae water slurry) to optimize carbohydrate content when necessary. Determining FAME measurements may be indicative of whether algae have been cultivated to a confluency (growth amount) adequate to begin harvesting. In all instances, real-time or near real-time understanding of these critical cultivation characteristics at one or more times during the cultivation process can permit quick corrective action to optimize biofuel production. Corrective action may include, but is not limited to, adjusting one or more cultivation parameters of the cultivating algae slurry, such as pH, salinity, temperature, nutrient media composition, slurry flow rate (e.g., turbidity), and the like, and any combination thereof. For example, such corrective action may be taken upon detection of the modified electromagnetic radiation and/or based on generated output signals indicative of one or more critical cultivation characteristics (see FIG. 1).

The MOC sensors of the present disclosure comprise an MOE that is tailored to a particular strain of algae in order to measure in-situ critical cultivation characteristics thereof, while otherwise remaining blind to any potential spectral interferents. That is, the MOE is calibrated to a particular algae strain and a particular critical cultivation characteristic thereof based on specific optical patterns produced from that characteristic, thereby "fingerprinting" said characteristic in an otherwise complex composition. Accordingly, a separate MOC sensor may be tailored for each particular critical cultivation characteristic, wherein each MOC sensor comprises a single MOE. Alternatively, a single MOC sensor may comprise a plurality of MOEs, in which each MOE is calibrated to a specific critical cultivation characteristic of a specific algae strain (e.g., where the MOEs are rotatable or otherwise swappable or otherwise exposed to a cultivating algae water slurry simultaneously). One of ordinary skill in the art, with the benefit of the present disclosure, will recognize suitable means to produce the calibrated MOE(s) of the present disclosure, particularly dependent upon the desired algae strain selected.

In one or more aspects of the present disclosure, the MOE(s) of the MOC sensors of the present disclosure are calibrated to detect in-situ the critical cultivation characteristics of any of the algae strains discussed hereinabove. In more particular aspects, the MOE(s) of the MOC sensors of the present disclosure are calibrated to detect in-situ the critical cultivation characteristics of unmodified and/or bio-engineered (genetically modified) algae strains, including any of those listed above without limitation. For example, in one or more aspects, the MOE(s) of the MOC sensors of the present disclosure are calibrated to detect in-situ the critical cultivation characteristics of unmodified and/or bio-engineered (genetically modified) algae strains of the order Chlorellales, such as those listed above including, for example, *Auxenochlorella, Chlorella, Compactochlorella, Leptochlorella, Marinichlorella, Nannochloris, Nanochlorum, Parachlorella, Planktochlorella, Psuedochlorococcum, Psuedochloris, Psuedochlorella, Tetrachlorella,* and *Zoochlorella* algae species, and any combination thereof.

Figure 1:
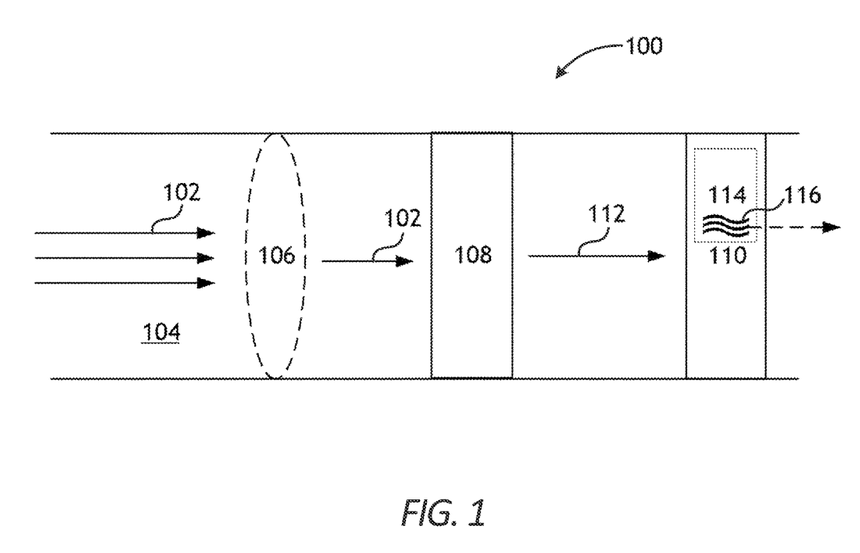
FIG. 1 is a block diagram of a multivariate optical computing sensor for use in one or more aspects of the present disclosure.

FIG. 1 is a block diagram of an MOC sensor 100 for use in one or more aspects of the present disclosure. Electromagnetic radiation 102 (referred to with reference to FIG. 1 as light 102), which may include any type of electromagnetic radiation, without limitation, as described herein, emanating from a cultivating algae water slurry within fluid flow path 104 comprises spectral information pertaining to the various specific constituents therein. The light 102 comprises spectra specific to the critical cultivation characteristic(s) of interest (e.g., depending on the number of MOEs in the MOC sensor), as well as other spectra corresponding to background constituents. The light 102 may be obtained by illumination from natural sunlight impinging upon a closed or open cultivation system. Alternatively or in addition, and while not shown, the cultivating algae water slurry may be illuminated by incident electromagnetic radiation using an integrated light source (e.g., a laser, light emitting diode, and the like) to obtain light 102, which may be within or outside of fluid flow path 104. As used herein, the term "fluid flow path," and grammatical variants thereof, refers to the movement of a flowable composition (i.e., may include one or more liquids comingled with gaseous and/or solid matter) between a first point and a second point, which need not be linear.

Optionally, the MOC sensor 100 may include one or more optical elements 106 to restrict, condition, or otherwise filter optical wavelengths that are not related to the particular desired spectral region (i.e., the electromagnetic spectral pattern) for the critical cultivation characteristic being targeted. That is, the one or more optional optical elements 106 may be used to define a desired spectral region. In one or more aspects, the optical element 106 may include, but is not limited to, irises, apertures, lenses, mirrors, and the like to direct and/or shape the light 102 optical wavelengths' cross-section to optimize optical throughput to MOE 108, thereby increasing the optical signal to noise ratio.

Light 102, which may or may not impinge optional optical element 106, encounters MOE 108. MOE 108 is calibrated to distinguish the electromagnetic spectral pattern information specific to the critical cultivation characteristic of interest for a specific algal species strain. MOE 108, encoded with the characteristic specific prediction spectral pattern, multiplies light 102 by its designed transmittance value at each wavelength to generate modified light 112. The modified electromagnetic radiation 112 (referred to with reference to FIG. 1 as modified light 112) thereafter is conveyed and detected by detector 110 (e.g., a broad band detector), thereby integrating modified light 112, and generating an output signal 116 indicative of a cultivation characteristic, such as a critical cultivation characteristic. For example, the output signal 116 generated by the detector 110 may be indicative (e.g., proportional) to the concentration of the critical cultivation characteristic for which the MOE 108 was calibrated.

The detector 110 may be equipped with a control unit 114 comprising a processor and memory having instructions stored therein for storing the output signal 116 data to a data storage unit. The data storage unit may store a finite amount of output signal 116 data over the period of time in which the MOC sensor is performing measurements (i.e., for the duration in which it is exposed to a cultivating algae water slurry), which can thereafter be downloaded by a wired communication link (e.g., USB connection, serial cable connection, and the like) to an external computing system (not shown) for further analysis. Alternatively, the control unit 114 may be further equipped with a transmitter unit for wireless transmission of the output signal 116 data (dashed arrow) to an external computing system (having an appropriate receiver), such as by way of a sonar communication link, an optical communication link, an infrared communication link, an RF communication link, a BLUETOOTH® communication link, and the like, and any combination thereof. The transmitter unit may be used to transmit the finite amount of output signal 116 data obtained over the period of time in which the MOC sensor is performing measurements to the external computing system. Alternatively, output signal 116 data may be transmitted wirelessly at periodic intervals (e.g., every 10 seconds, every 30 seconds, every 1 minute, 5 minutes, 10 minutes, and the like) to an external computing system obtain real-time or substantially real-time data analysis, including real-time or substantially real-time periodic intervals (e.g., every 0.001 seconds, every 0.01 seconds, every 0.1 seconds, every 1 second, and the like).

In one or more aspects, the output signal 116 data downloaded or transmitted by the control unit 114 of the detector 110 may be a signal indicative of the concentration of the measured critical cultivation characteristic of interest, or indicative of other meaningful properties, such as physical properties. Once received by the external computing system, an algorithm may be used to convert the received output signal 116 data into concentration and/or other meaningful properties. In additional or alternative aspects, the memory within the control unit 114 may comprise instructions for executing an algorithm capable of converting the output signal 116 data into concentration and/or other meaningful properties. In such instances, the transmitted output signal 116 data may be actual concentration (e.g., concentration of TOC, concentration of total carbohydrate, concentration of FAME, and the like) and/or other meaningful concentrations or physical properties, such as photosynthetic capacity, chlorophyll concentration, chlorophyll-type ratio (e.g., chlorophyll A v. chlorophyll B), phase, density, electromagnetic radiation scatter amount, turbidity, color, and the like, and any combination thereof.

The selected platform for deployment of the MOC sensors of the present disclosure may vary depending on a number of factors, including the particular cultivation system being assayed (e.g., open or closed cultivation system), for example. The MOC sensor is rather small in size and can accordingly be deployed using a variety of deployment platforms.

In various aspects, the deployment platform for the MOC sensor may be a stationary platform, such as stationary upon a wall or other surface of an open or closed cultivation system which would allow the MOC sensor to come into contact with a cultivating algae water slurry. In various aspects the MOC sensor may be deployed on a conveyance, such as a weighted conveyance, particularly if the cultivation system is an open cultivation system. That is, the MOC sensor may be placed at a particular location within the open cultivation system utilizing the conveyance and allowing the MOC sensor to take measurements at a stationary position, which may be otherwise moveable vertically or horizontally by moving the location of the conveyance. The conveyance may also be adjusted to allow measurements at various depths of a cultivating algae water slurry and/or may be flexible to allow the MOC sensor to allow un-restrictive movement of the MOC sensor.

The stationary and/or conveyance deployment platforms may permit multiple MOC sensors to be placed in-line to provide multiple measurements for one or more critical cultivation characteristics of interest for a single algae strain. The term "in-line," and grammatical variants thereof, refers to MOC sensors positioned such that measurements can be made at different locations along a flow pattern of a cultivation system (i.e., at locations along the flowing direction of the cultivating algae water slurry), and need not be linear. The stationary and/or conveyance deployed MOC sensors may be networked together to provide signal data associated with one or more cultivation characteristics of interest to a centralized external computing system, such as described hereinabove.

In alternative or additional aspects, the deployment platform for the MOC sensor may be an autonomous passive vehicle, such as a buoyancy-controlled passive float and/or an autonomous active vehicle, such as a buoyancy-driven autonomous underwater glider (AUG), an autonomous benthic vehicle (ABV) (e.g., a rover, crawler, or hopper), an autonomous amphibious vehicle (e.g., for traversing water and land), any of which may be incorporated with an aerial (air flight) capability (e.g., to permit autonomous movement between various cultivation systems, for example), and the like. The use of an autonomous vehicle deployment platform for the MOC sensor may reduce the need for multiple MOC when using stationary and/or conveyance sensor platforms because the autonomous vehicle can sweep a large portion, if not all, of the area of the cultivation system, particularly if the autonomous vehicle is an active autonomous vehicle using one or more navigation sensors (e.g., global positioning system). Moreover, an autonomous vehicle deployment platform may permit inclusion of other environmental measurement sensors for determining other cultivation characteristics, such as those described hereinabove, and may further be equipped to obtain one or more samples of the cultivating algae water slurry for physical testing, including comparison of the MOC sensor data against data obtained from traditional analytical methods (e.g., wet chemistry or spectrometer-based analysis).

Passive autonomous vehicles may float along with the flow pattern of the particular cultivation system, whereas the active autonomous vehicles may be driven (controlled) by a computer system. For example, active autonomous vehicles may be used to measure areas within a cultivation system that are particularly defined, such as areas having a greater concentration of algae growth due to the configuration of the cultivation system. And they are not limited to a single measurement at a single location, but can be programmed to measure critical cultivation characteristics at a plurality of locations. Additionally, the active autonomous vehicles may be capable of being bottomed and thus well suited to measure areas that are otherwise unreachable by passive autonomous vehicles. It is to be understood that an active autonomous vehicle that is buoyant may be otherwise allowed to act as a passive autonomous vehicle by ceasing control of the vehicle by the computer system and allowing it to passively float.

One or more MOC sensors may be integrated with a passive and/or active autonomous vehicle by a variety of means, and may depend on the particular autonomous vehicle selected. For example, an MOC sensor may be physically affixed (e.g., by mechanical or adhesive means) to an outer portion of the autonomous vehicle, such as a dip-probe. In other instances, the MOC sensor may be provided within a housing of the autonomous vehicle and a flow inlet provided to allow a cultivating algae water slurry to enter into the flow path of the MOC sensor and exit from a flow outlet after interacting with the detector 110 (FIG. 1) without influencing the operability of the autonomous vehicle.

The combination of a conveyance, a passive autonomous vehicle, and/or an active autonomous vehicle may be used in accordance with various aspects of the present disclosure, without limitation. Each may include one or more MOC sensors for measurement of one or more critical cultivation characteristics.

Accordingly, the MOC sensors described herein may independently, without human intervention, such as is needed for traditional laboratory assaying, interrogate a cultivating algae slurry to provide measurements pertaining to critical cultivation characteristics of a particular algae strain. The MOC sensors may be held stationary at a particular location or incorporated into an autonomous passive or active vehicle, including any combination thereof.

The present disclosure provides, among others, the following aspects, each of which may be considered as optionally including any alternate thereof:

Clause 1: A multivariate optical computing sensor comprising: a first multivariate optical element calibrated to independently measure an electromagnetic spectral pattern of a first cultivation characteristic of an algae strain in a cultivating algae water slurry; and a detector for receiving modified electromagnetic radiation from the first multivariate optical element and generating an output signal indicative of the first cultivation characteristic.

Clause 2: The multivariate optical computing sensor of Clause 1, wherein the first cultivation characteristic is total organic carbon, total carbohydrate, or fatty acid methyl esters.

Clause 3: The multivariate optical computing sensor of any of the preceding Clauses, wherein the algae strain is bio-engineered.

Clause 4: The multivariate optical computing sensor of any of the preceding Clauses, wherein the detector further comprises a control unit including a data storage unit to store the output signal indicative of the first cultivation characteristic.

Clause 5: The multivariate optical computing sensor of any of the preceding Clauses, wherein the detector further comprises a control unit including a transmitter unit to wirelessly transmit through a wireless transmission link the output signal indicative of the first cultivation characteristic.

Clause 6: The multivariate optical computing sensor of Clause 5, wherein the wireless transmission link is selected from the group consisting of a sonar communication link, an optical communication link, an infrared communication link, an RF communication link, a BLUETOOTH® communication link, and any combination thereof.

Clause 7: The multivariate optical computing sensor of any of the preceding Clauses, further comprising an integrated light source.

Clause 8: The multivariate optical computing sensor of any of the preceding Clauses, further comprising at least a second multivariate optical element that is calibrated to independently measure an electromagnetic spectral pattern of a second cultivation characteristic of the algae strain in the cultivating algae water slurry, wherein the second cultivation characteristic is different than the first cultivation characteristic.

Clause 9: The multivariate optical computing sensor of Clause 8, further comprising at least a third multivariate optical element that is calibrated to independently measure an electromagnetic spectral pattern of a third cultivation characteristic of the algae strain in the cultivating algae water slurry, wherein the third cultivation characteristic is different than the first cultivation characteristic and the second cultivation characteristic.

Clause 10: A method comprising: deploying a multivariate optical computing sensor into a cultivating algae water slurry comprising an algae strain, the multivariate optical computing sensor comprising: a first multivariate optical element calibrated to independently measure an electromagnetic spectral pattern of a first cultivation characteristic of the algae strain in the cultivating algae water slurry; and a detector; receiving, by the first multivariate optical element, electromagnetic radiation from the cultivating algae water slurry; distinguishing, by the first multivariate optical element, the electromagnetic spectral pattern of the first cultivation characteristic, thereby producing the modified electromagnetic radiation; and detecting, by the detector, the modified electromagnetic radiation; and generating, by the detector, output signals indicative of the first cultivation characteristic.

Clause 11: The method of Clause 10, further comprising deploying the multivariate optical computing sensor to a stationary location within the cultivating algae water slurry.

Clause 12: The method of Clause 10 or 11, further comprising deploying the multivariate optical computing sensor in the cultivating algae water slurry on or within an autonomous vehicle.

Clause 13: The method of Clause 12, wherein the autonomous vehicle is an autonomous passive vehicle or an autonomous active vehicle.

Clause 14: The method of Clauses 10 to 13, further comprising cultivating the cultivating algae water slurry in an open cultivation system or a closed cultivation system.

Clause 15: The method of Clauses 10 to 14, wherein the detector further comprises a control unit including a data storage unit, and further comprising storing the output signal indicative of the first cultivation characteristic by the data storage unit.

Clause 16: The method of Clauses 10 to 15, wherein the detector further comprises a control unit including a transmitter unit, and further comprising wirelessly transmitting through a wireless transmission link the output signal indicative of the first cultivation characteristic.

Clause 17: The method of Clauses 10 to 16, further comprising adjusting at least one cultivation parameter based on the generated output signal indicative of the first cultivation characteristic.

Clause 18: The method of Clause 17, wherein the at least one cultivation parameter is selected from the group consisting of pH, salinity, temperature, nutrient media composition, slurry flow rate, and any combination thereof.

Clause 19: The method of Clauses 10 to 18, wherein the first cultivation characteristic is total organic carbon, total carbohydrate, or fatty acid methyl esters.

Clause 20: The method of Clauses 10 to 19, wherein the algae strain is bio-engineered.

To facilitate a better understanding of aspects of the present disclosure, the following examples of preferred or representative aspects are given. In no way should the following examples be read to limit, or to define, the scope of the disclosure.

EXAMPLES

Example 1

In this Example, near infrared (NIR) spectroscopic data was used to model the critical cultivation characteristic FAME collected in deplete and replete growth phases of bio-engineered algae strain Sample 1, a bio-engineered algae strain of the order Chlorellales. NIR data were collected from algal aqueous solutions pulled from several cultivation systems over time during replete and deplete phases. Spectra were recorded in transmission mode. NIR data were imported into commercial software for pretreatment. NIR data were modeled using Partial Least Squares using a leave one out cross validation. Models were validated with a number of spectra left out to develop an understanding of theoretical MOE performance. A variable selection algorithm was used to optimize models that performed over wide spectral regions to determine which spectral regions could be leveraged to develop subsequent MOE designs.

Figure 2:
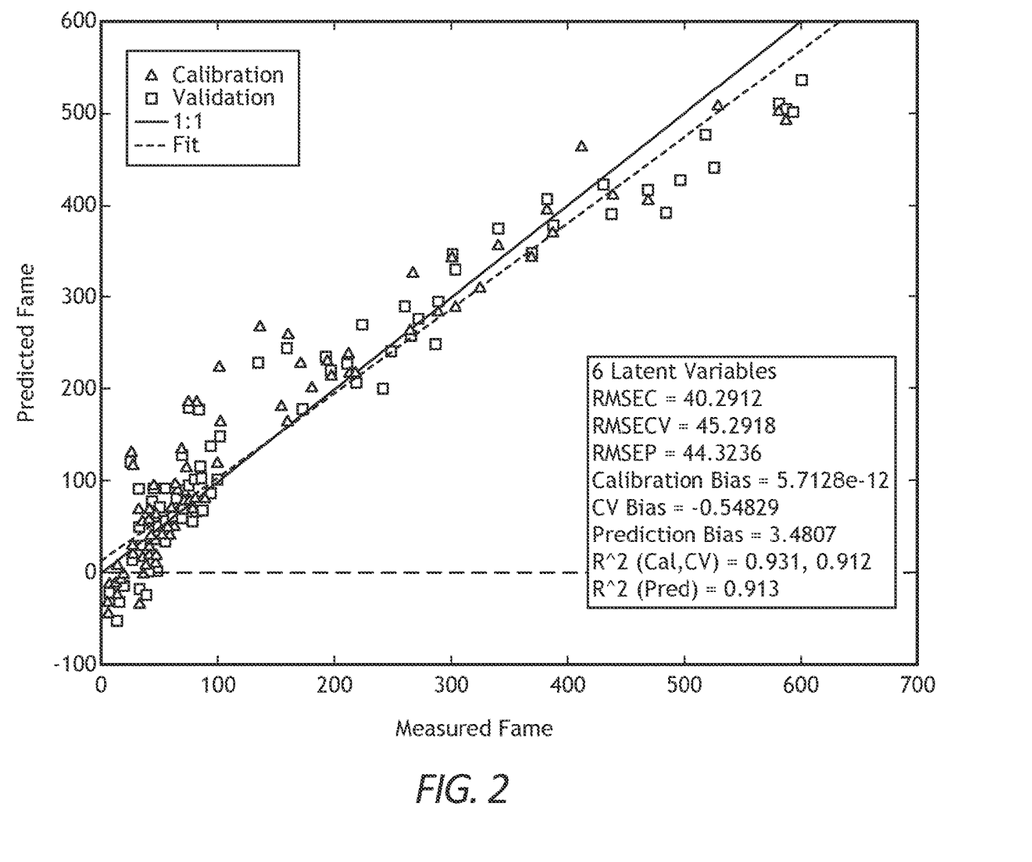
FIGS. 2-4 are near infrared spectrographs predicting critical cultivation characteristics for modeling multivariate optical computing sensors for use in one or more aspects of the present disclosure.

An exemplary result is shown in FIG. 2. In this example, a 6 principal component model was developed that has a model error estimate (RMSEP) of approximately 44 μm/mL. As shown, NIR spectroscopy may be used to model the critical cultivation characteristic with sufficient sensitivity (e.g., FAME in this example).

Example 2

In this Example, NIR spectroscopic data was used to model the critical cultivation characteristics TOC and FAME collected in deplete and replete growth phases of combined algae strains Sample 2 and Sample 3, both bio-engineered algae strains of the order Chlorellales, as performed in Example 1 above.

Figure 3:
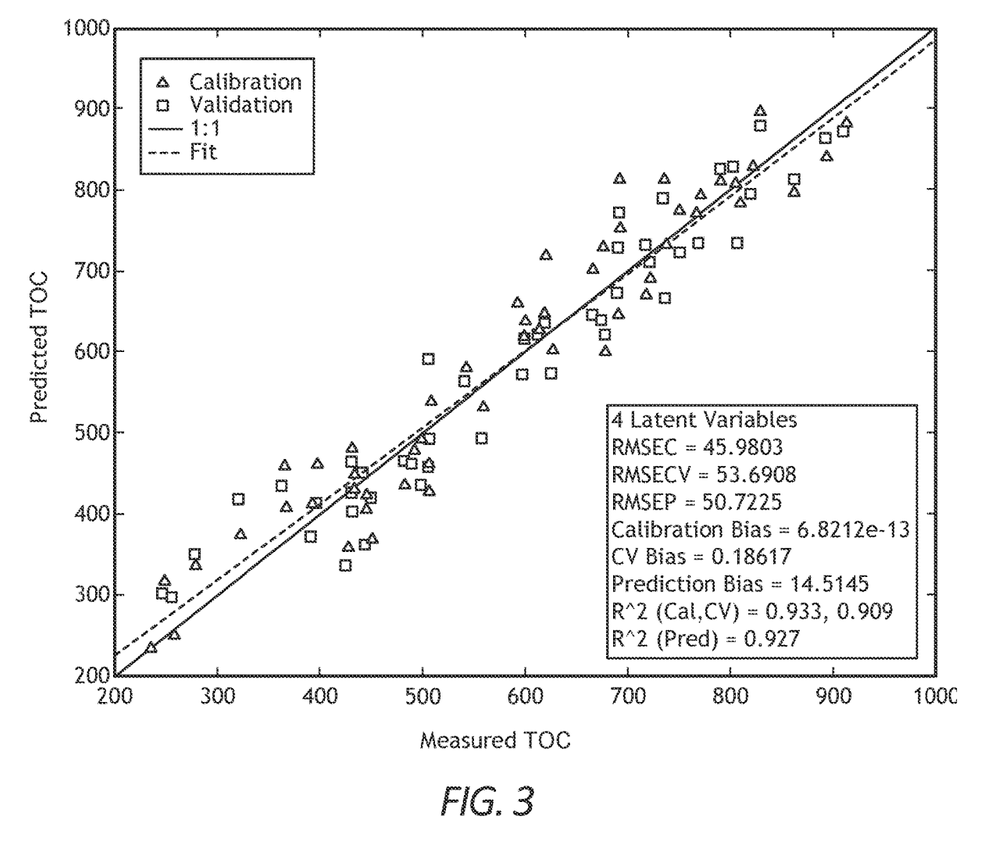
Figure 4:
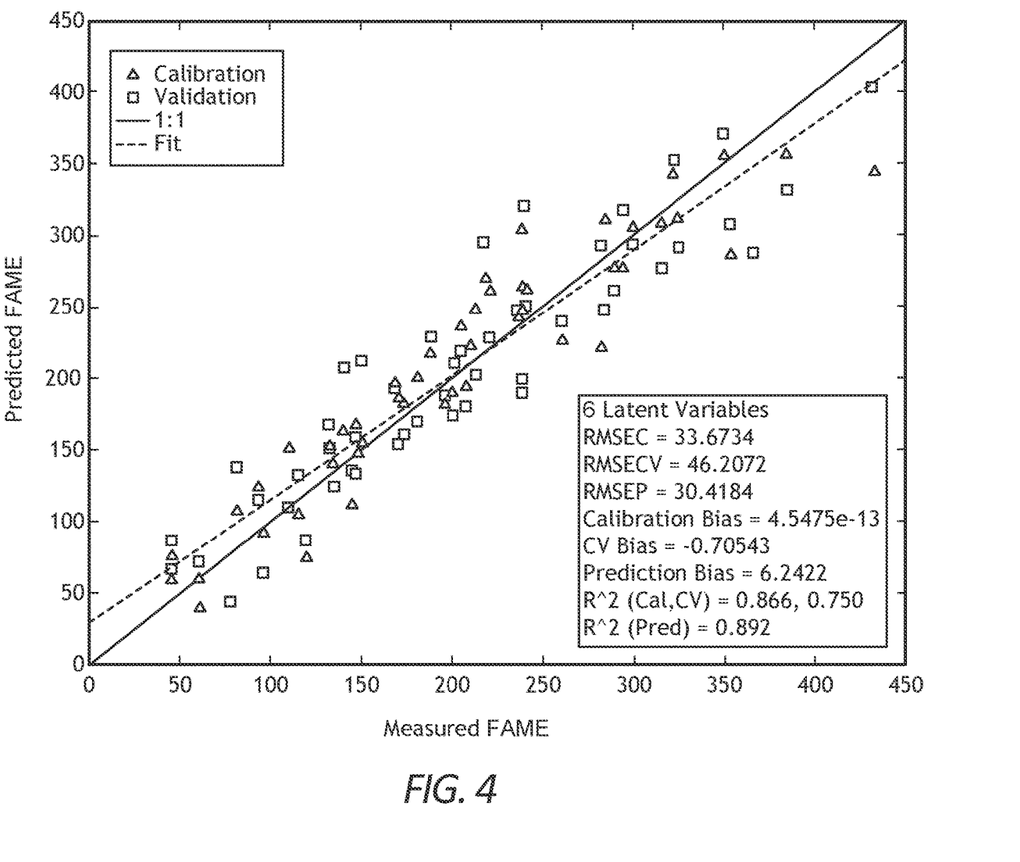

The results of the TOC data are shown in FIG. 3 and the results of the FAME data are shown in FIG. 4. As shown, like in Example 1, NIR spectroscopy may be used to model the critical cultivation characteristic with sufficient sensitivity (e.g. TOC and FAME). The spectral regions used in Example 2 are the same as shown in Example 1. The model error is improved compared to Example 1 and demonstrates that the model can be successfully used for genetically similar algae of different strains (i.e., combined algae strains Sample 2 and Sample 3) with NIR spectroscopy. Accordingly, information gained through traditional NIR chemometric modeling is useful in guiding the design of MOEs for the MOC sensors described in the present disclosure, such as spectral wavelength region and prediction performance.

Example 3

Figure 5:
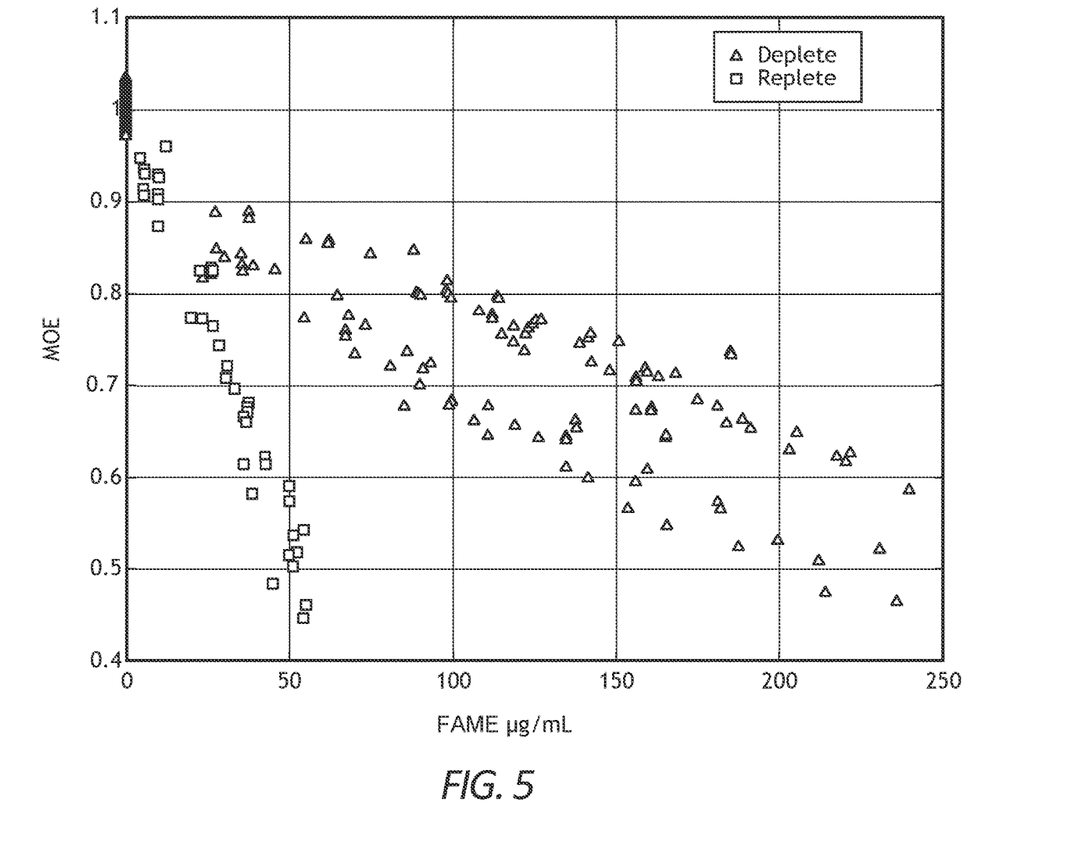
FIG. 5 is a graph showing detector signal change from a multivariate optical computing sensor from samples containing a range of fatty acid methyl ester concentrations for use in one or more aspects of the present disclosure.

In this Example, a MOE sensitive to FAME for algae strain Sample 4, a bio-engineered algae strain of the order Chlorellales, was developed and evaluated. The MOE sensor detector signal was evaluated using algae strain Sample 4 over time during several replete and deplete phases against a known FAME concentration control (x-axis). The results show that the MOE signal varied in proportion to the FAME concentration. The results are provided in FIG. 5. As shown, the developed FAME MOE sensitive to FAME concentration, again demonstrating that MOEs for MOC sensors may be used to effectively evaluate at least critical cultivation characteristics.

Example 4

Figure 6:
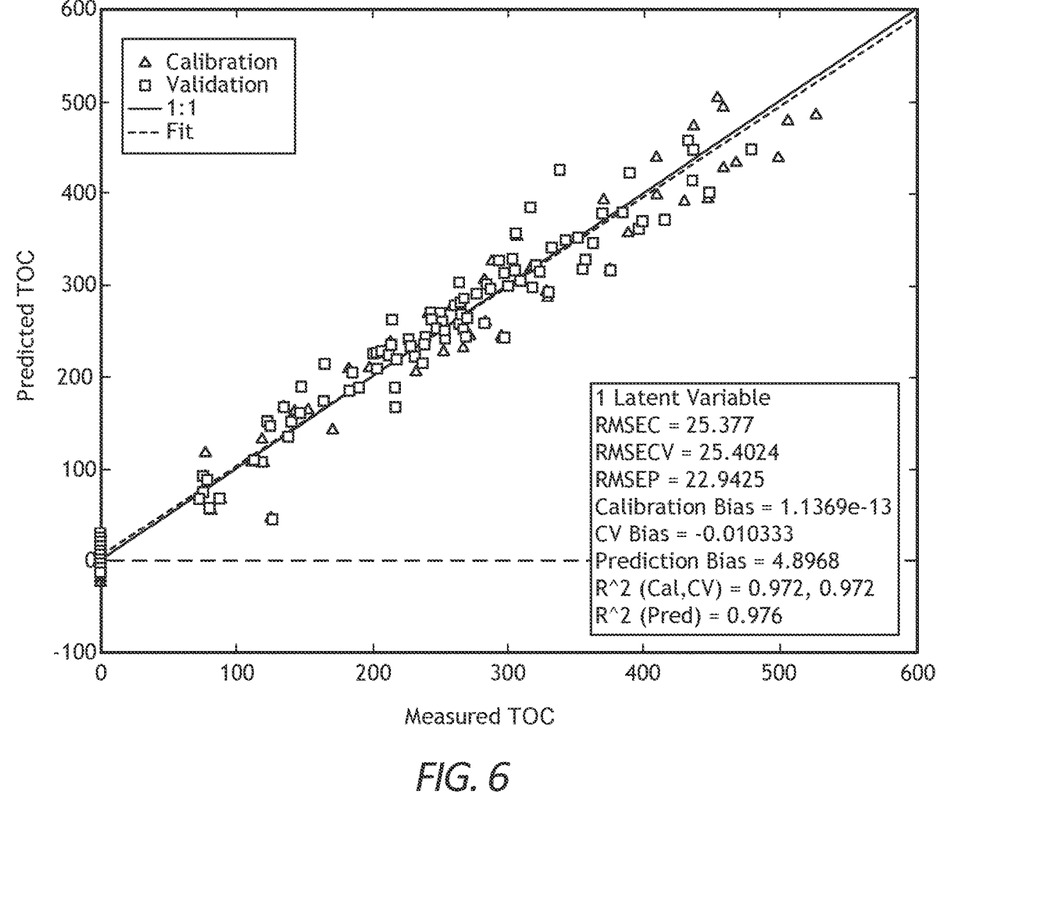
FIG. 6 is a calibration plot generated modeling the multivariate optical computing sensors for total organic carbon for use in one or more aspects of the present disclosure.

In this Example, an MOC-based system was used to model the critical cultivation characteristic TOC collected in deplete and replete growth phases of combined algae strain Sample 5, a bio-engineered algae strain of the order Chlorellales. The MOC-based system contained 2 MOEs that were sensitive to TOC. The MOE signals obtained from a set of calibration samples with a wide range of TOC were combined and modeled to generate a prediction for TOC. The model was validated on a separate set of samples. In this Example, calibration coefficients were applied to convert the MOE signals (in volts) to TOC concentration (TOC in μg/mL). The results are shown in FIG. 6 (which may be compared to FIG. 3) and demonstrate that the MOC-based modeling system has approximately half the error prediction compared to the NIR spectroscopic system. Accordingly, information gained through MOC-based modeling is useful in guiding the design of MOEs for the MOC sensors described in the present disclosure, such as spectral wavelength region and prediction performance.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more elements are presented herein. Not all features of a physical implementation are described or shown in this application for the sake of clarity. It is understood that in the development of a physical aspect incorporating one or more elements of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present disclosure is well adapted to attain the ends and advantages mentioned as well as those that are inherent therein. The particular examples and configurations disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present disclosure. The aspects illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A multivariate optical computing sensor comprising:
    a first multivariate optical element calibrated to independently measure an electromagnetic spectral pattern of a first cultivation characteristic of a single algae strain in a cultivating algae water slurry; and
    a detector for receiving modified electromagnetic radiation from the first multivariate optical element and generating an output signal indicative of the first cultivation characteristic, wherein the first cultivation characteristic is total organic carbon, total carbohydrate, or fatty acid methyl esters.

2. The multivariate optical computing sensor of claim 1, wherein the first cultivation characteristic is total carbohydrate.

3. The multivariate optical computing sensor of claim 1, wherein the first cultivation characteristic is fatty acid methyl esters.

4. The multivariate optical computing sensor of claim 1, wherein the detector further comprises a control unit including a data storage unit to store the output signal indicative of the first cultivation characteristic.

5. The multivariate optical computing sensor of claim 1, wherein the detector further comprises a control unit including a transmitter unit to wirelessly transmit through a wireless transmission link the output signal indicative of the first cultivation characteristic.

6. The multivariate optical computing sensor of claim 5, wherein the wireless transmission link wirelessly transmits the output signal at periodic intervals.

7. The multivariate optical computing sensor of claim 1, further comprising a second multivariate optical element that is calibrated to independently measure an electromagnetic spectral pattern of a second cultivation characteristic of the single algae strain in the cultivating algae water slurry, wherein the second cultivation characteristic is different than the first cultivation characteristic.

8. The multivariate optical computing sensor of claim 7, wherein the second cultivation characteristic is photosynthetic capacity, lipid concentration, or phase.

9. The multivariate optical computing sensor of claim 7, further comprising at least a third multivariate optical element that is calibrated to independently measure an electromagnetic spectral pattern of a third cultivation characteristic of the single algae strain in the cultivating algae water slurry, wherein the third cultivation characteristic is different than the first cultivation characteristic and the second cultivation characteristic.

10. A method comprising:
    deploying, in situ, a multivariate optical computing sensor into a cultivating algae water slurry comprising a single algae strain, the multivariate optical computing sensor comprising:
    a first multivariate optical element calibrated to independently measure an electromagnetic spectral pattern of a first cultivation characteristic of the single algae strain in the cultivating algae water slurry;
    a second multivariate optical element calibrated to independently measure an electromagnetic spectral pattern of a second cultivation characteristic of the single algae strain in the cultivating algae water slurry, wherein the second cultivation characteristic is different than the first cultivation characteristic; and
    a detector;
    receiving, by the first multivariate optical element and the second multivariate optical element, electromagnetic radiation from the cultivating algae water slurry;
    distinguishing, by the first multivariate optical element and the second multivariate optical element, the electromagnetic spectral pattern of the first cultivation characteristic and the second cultivation characteristic, thereby producing the modified electromagnetic radiation; and
    detecting, by the detector, the modified electromagnetic radiation; and
    generating, by the detector, output signals indicative of the first cultivation characteristic and the second cultivation characteristic.

11. The method of claim 10, further comprising determining a measurement of fatty acid methyl esters to determine whether the cultivating algae slurry has reached confluency.

12. The method of claim 10, further comprising deploying the multivariate optical computing sensor in the cultivating algae water slurry on or within an autonomous vehicle, wherein the autonomous vehicle is configured to obtain one or more samples of the cultivating algae water slurry.

13. The method of claim 12, wherein the autonomous vehicle obtains one or more samples of the cultivating algae water slurry for traditional spectrometer analysis such as to compare data derived from the multivariate optical computing sensor against the traditional spectrometer analysis.

14. The method of claim 10, further comprising cultivating the cultivating algae water slurry in a closed cultivation system.

15. The method of claim 10, wherein the detector further comprises a control unit including a data storage unit, and further comprising storing the output signals indicative of the first cultivation characteristic and the second cultivation characteristic by the data storage unit.

16. The method of claim 10, wherein the detector further comprises a control unit including a transmitter unit, and further comprising wirelessly transmitting through a wireless transmission link the output signals indicative of the first cultivation characteristic and the second cultivation characteristic.

17. The method of claim 10, further comprising adjusting at least one cultivation parameter based on the generated output signal indicative of the first cultivation characteristic or the second cultivation characteristic.

18. The method of claim 17, wherein the at least one cultivation parameter is selected from the group consisting of pH, salinity, temperature, nutrient media composition, slurry flow rate, and any combination thereof.

19. The method of claim 10, wherein the first cultivation characteristic is total organic carbon, total carbohydrate, or fatty acid methyl esters.

20. The method of claim 13, wherein the multivariate optical computing sensor and the second multivariate optical computing sensor are networked together to provide the output signals associated with the first cultivation characteristic and the second cultivation characteristic to a centralized computing system.

\* \* \* \* \*